(12) United States Patent
Willcox et al.

(10) Patent No.: US 8,741,878 B2
(45) Date of Patent: Jun. 3, 2014

(54) PETROLEUM JELLY-FREE UNGUENT COMPOSITIONS COMPRISING VITAMIN D COMPOUNDS AND OPTIONALLY STEROIDAL ANTI-INFLAMMATORY AGENTS

(75) Inventors: Nathalie Willcox, Magagnosc (FR); Nathalie Barthez, Saint Laurent du Var (FR); Karine Nadau-Fourcade, Villeneuve Loubet (FR); Claire Mallard, Mougins (FR)

(73) Assignee: Galderma S.A., Cham (CH)

( * ) Notice: Subject to any disclaimer, the term of this patent is extended or adjusted under 35 U.S.C. 154(b) by 634 days.

(21) Appl. No.: 12/457,029

(22) Filed: May 29, 2009

(65) Prior Publication Data

US 2009/0298801 A1 Dec. 3, 2009

Related U.S. Application Data

(63) Continuation of application No. PCT/FR2007/052432, filed on Nov. 30, 2007.

(30) Foreign Application Priority Data

Nov. 30, 2006 (FR) ...................................... 06 55205

(51) Int. Cl.
*A01N 45/00* (2006.01)
(52) U.S. Cl.
USPC ........................... 514/167; 514/171; 424/400
(58) Field of Classification Search
None
See application file for complete search history.

(56) References Cited

U.S. PATENT DOCUMENTS

| | | | |
|---|---|---|---|
| 2005/0281848 | A1 | 12/2005 | Zanutto et al. |
| 2006/0009426 | A1 | 1/2006 | Jomard et al. |
| 2007/0135379 | A1 | 6/2007 | Mallard et al. |

FOREIGN PATENT DOCUMENTS

| | | | |
|---|---|---|---|
| EP | 1051974 | A1 | 11/2000 |
| FR | 2848454 | A1 | 6/2004 |
| FR | 2867682 | A1 | 9/2005 |
| WO | WO 00/64450 | A1 | 11/2000 |
| WO | WO 02/34235 | A1 | 5/2002 |

*Primary Examiner* — Frederick Krass
*Assistant Examiner* — Nannette Holloman
(74) *Attorney, Agent, or Firm* — Dentons US LLP

(57) ABSTRACT

Novel compositions in petroleum jelly-free unguent form, in particular for topical application, contain a vitamin D compound and optionally an active agent of the family of steroidal anti-inflammatory agents.

24 Claims, No Drawings

PETROLEUM JELLY-FREE UNGUENT COMPOSITIONS COMPRISING VITAMIN D COMPOUNDS AND OPTIONALLY STEROIDAL ANTI-INFLAMMATORY AGENTS

CROSS-REFERENCE TO EARLIER APPLICATIONS

This application is a continuation of PCT/FR 2007/052432, filed Nov. 30, 2007 and designating the United States (published in the French language on Jun. 5, 2008 as WO 2008/065316 A2; the title and abstract were also published in English), which claims foreign priority of FR 06/55205, filed Nov. 30, 2006, each hereby expressly incorporated by reference in its entirety and each assigned to the assignee hereof.

BACKGROUND OF THE INVENTION

1. Technical Field of the Invention

The present invention relates to novel compositions in the form of anhydrous unguents containing no petroleum jelly, in particular for topical application, comprising a vitamin D derivative optionally combined with an active agent of the family of steroidal anti-inflammatory agents.

2. Description of Background and/or Related and/or Prior Art

Vitamin D and its derivatives are generally administered in dermatology in the treatment of psoriasis because they limit the excessive production of skin cells on the affected surfaces and have proven advantageous for the treatment of this condition which is characterized, in particular, by the presence of thick, squamous and dry lesions.

It is known that a number of active ingredients having an advantageous therapeutic activity are sensitive to oxidation and undergo chemical degradation leading to a substantial loss of their activity in the presence of water.

In particular, vitamin D or certain vitamin D derivatives are unstable in an acidic environment (they exhibit maximum stability at pH values in the region of 8).

Furthermore, it is advantageous to administer several classes of active ingredients, in particular for the treatment of dermatological pathologies. This also makes it possible to increase the efficacy of the active ingredients and to reduce their toxicity (Cunliffe W. J., *J. Dermato. Treat.*, 2000, 11 (suppl. 2) S13-S14). Here again, a problem of long-term chemical stability is frequently encountered during the formulation of two active agents in the same vehicle. This is in particular the case for the combination of a vitamin D derivative with a corticoid. Indeed, certain corticosteroids are unstable in a basic environment (they exhibit maximum stability at a pH of about 4 to 6). This combination is nevertheless advantageous in the treatment of psoriasis.

Consequently, in the case of a combination, it is advisable to formulate the combination of vitamin D or of a vitamin D derivative with an active agent of the family of steroidal anti-inflammatory agents in compositions of the anhydrous type.

The currently commercially available anhydrous compositions, allowing the formulation of water-sensitive active ingredients, while providing them with good chemical stability, are generally unguent-type compositions consisting mainly of petroleum jelly. However, the use of petroleum jelly is not satisfactory for the following reasons:

after application, certain compositions comprising petroleum jelly are felt to be sticky and greasy, and are furthermore shiny. The fatty residue left on the skin prevents patients with psoriasis from putting their clothes back on after treatment without the risk of leaving greasy marks on them, which does not necessarily encourage patients to follow their treatment. Noncompliance with the prescribed treatment is one of the main causes of failure: the article "*Patients with psoriasis and their compliance with medication*, Richards et al, *J. Am. Acad Dermatol.*, October 1999, p. 581-583" states that nearly 40% of patients with a chronic disease such as psoriasis do not follow their treatment. The characteristics of the vehicle used in the pharmaceutical compositions are directly linked to the patient's compliance with their treatment;

moreover, the formulation of compositions in the form of petroleum jelly-based unguents requires compounds and specific conditions. Indeed, petroleum jelly is solid at room temperature, and has a melting point greater than 40° C. To be able to mix it with other compounds, it is necessary to formulate it in the liquid state, and therefore to produce the compositions at temperatures greater than 40° C. This is in particular the case described in WO2006/005842. However, such a method has as a disadvantage the formation of a phenomenon of encrusting. Indeed, the more rapid cooling of the outside of the composition compared with its center causes its abnormal hardening (encrusting), which has the effect of slowing, or even preventing, a perfect homogenization;

finally, the formulation of vitamin D derivatives, in particular of calcitriol, and of corticoids, in particular clobetasol, is delicate because of the sensitivity of these active agents to heat.

SUMMARY OF THE INVENTION

The present invention features petroleum jelly-free anhydrous pharmaceutical compositions, suited for topical application, which have a viscosity equivalent to that of petroleum jelly-containing unguents, which are easy to prepare, which provide a good chemical stability of the active agents and in which certain volatile compounds may be included. The compositions according to the invention have in particular these advantages by virtue of their mode of formulation. The present invention therefore also features the particularly advantageous method of preparing such a composition, in which the step for incorporating the active agents is carried out at room temperature.

The present invention also features petroleum jelly-free anhydrous pharmaceutical compositions suited for topical application, exhibiting prolonged stability and allowing optimized release of the active agents while being very well tolerated.

This invention therefore features novel stable compositions in the form of anhydrous unguents containing no petroleum jelly, in particular for topical application, comprising at least one vitamin D compound. The compositions according to the invention may optionally contain at least one steroidal anti-inflammatory agent.

The expression "anhydrous" composition means a composition comprising a quantity of water less than or equal to 5% by weight relative to the total weight of the composition.

The expression stable composition means a composition which is chemically and physically stable.

The expression chemical stability means, in particular, that no degradation of the active agent is observed over time and at temperatures from 4° to 40° C. The expression physical stability means, in particular, that the compositions exhibit no reduction in viscosity over time and at temperatures from 4° to 40° C.

The expression unguent according to the invention means a thick composition at room temperature, commonly called "unguent, but also "ointment" or thick "cream" which comprises from 80 to 95% by weight relative to the total weight of the composition of hydrophobic compounds different from petroleum jelly. Such compounds are selected in particular from among liquid oils alone or as a mixture, it being possible for the said oils to be hydrocarbons, esters, vegetable oils and/or silicone oils, which are volatile or nonvolatile, and which may be gelled with lipophilic compounds which are solid at room temperature such as waxes, butter or fatty acid esters.

The expression thick means a composition having a final viscosity which is strictly greater than 30,000 cps at 25° C., the said viscosity being measured with the aid of a Brookfield RVDVII Rotor 18 at the speed of 5 rpm in 30 s. Preferably, the viscosity is in the region of 90,000 cps, measured at 25° C. with the aid of a Brookfield RVDVII+Rotor 4 at the speed of 30 rpm in 30 s.

Of course, one skilled in this art will adjust the parameters for the measurement of viscosity according to the composition according to the invention.

Herein, the expression room temperature means a temperature from 20° to 30° C.

DETAILED DESCRIPTION OF BEST MODE AND SPECIFIC/PREFERRED EMBODIMENTS OF THE INVENTION

The anhydrous nature of the unguent containing no petroleum jelly according to the invention makes it possible to avoid the instability of the vitamin D compound in an aqueous medium. Moreover, during application to the skin, it also makes it possible to slow the evaporation of water, and therefore increases the impermeability of the horny layer; the hydrophobic film formed thus promotes skin moisturization and the transfer of the active agents.

Thus, the anhydrous unguents according to the invention comprise:
  at least one vitamin D compound;
  glyceryl behenate and/or derivative and/or mixture thereof;
  optionally, at least one additional lipophilic thickener or gelling agent;
  at least one solvent for the active ingredients, the said solvent having a boiling point of greater than 40° C.;
  at least one fatty substance.

Preferably, as mentioned above, the unguents according to the invention substantially contain no petroleum jelly, i.e., comprise at most 1% by weight of petroleum jelly relative to the total weight of the composition.

The expression "vitamin D derivatives" means compounds which have biological properties similar to those of vitamin D, in particular properties of transactivation of vitamin D response elements (VDRE), such as an agonist or antagonist activity towards receptors for vitamin D or its derivatives. These compounds are generally not natural metabolites of vitamin D. There are in particular synthetic compounds comprising the vitamin D backbone with modifications on the side chains and/or also comprising modifications in the backbone itself. Compounds derived from vitamin D which are useful according to the invention thus comprise structural, for example biaromatic, analogues.

By way of illustration of vitamin D derivatives, particularly exemplary are calcipotriol, calcitriol or 1,25-dihydroxyvitamin $D_3$, doxercaciferol, secalcitol, maxacalcitol, seocalcitol, tacalcitol, paricalcitol, falecalcitriol, 1α,24S-dihydroxyvitamin D2, 1(S),3(R)-dihydroxy-20(R)-[((3-(2-hydroxy-2-propyl)phenyl)methoxy)methyl]-9,10-secopregna-5(Z),7(E),10(19)triene, {4-[6-ethyl-4'-(1-ethyl-1-hydroxypropyl)-2'-propylbiphenyl-3-yloxymethyl]-2-hydroxymethylphenyl}methanol and mixtures thereof.

According to a preferred embodiment of the invention, the vitamin D derivative is calcitriol.

As vitamin D derivatives which can be formulated according to the invention, the compounds described in WO 02/34235, WO 00/64450, EP1124779, EP1235824, EP1235777, WO 02/94754, WO 03/050067 and WO 00/26167 are also exemplary. The compounds described in WO 00/26167 relate to structural analogues of vitamin D which show a selective activity on cell proliferation and differentiation without exhibiting a hypercalcaemic character.

Advantageously, the quantity of vitamin D derivative is 0.00001 to 5% by weight relative to the total weight of the composition, preferably 0.0001 to 1% by weight and more particularly 0.0001 to 0.1% by weight.

According to an advantageous embodiment of the invention, the composition comprises, as second pharmaceutical active agent, a steroidal anti-inflammatory agent. Preferably, the agent is selected from the group consisting of betamethasone, clobetasol, clobetasone, desoxymethasone, diflucortolone, diflorasone, fluocinonide, flumethasone, fluocinolone, fluticasone, fluprednidene, halcinonide, hydrocortisone, mometasone, triamcinolone, their pharmaceutically acceptable esters and acetonides and mixtures thereof.

By way of examples of esters or acetonides, representative are those selected from the group consisting of 17-valerate, 17-propionate, 17,21-dipropionate, acetonide, acetonide-21-N-benzoyl-2-methyl-β-alaninate, acetonide-21-(3,3-dimethylbutyrate) and 17-butyrate.

According to a preferred embodiment of the invention, the steroidal anti-inflammatory agent is clobetasol 17-propionate (called clobetasol propionate in the present application).

Preferably, the composition comprises a quantity of steroidal anti-inflammatory agent from 0.0001 to 10% by weight relative to the total weight of the composition, preferably from 0.001 to 5%, more preferably still from 0.001 to 0.1% by weight.

The compositions according to the invention comprise glyceryl behenate, its derivatives or mixtures thereof. The expression glyceryl behenate means in particular, but not exclusively, glyceryl monobehenate, glyceryl dibehenate, tribehenin. The composition according to the invention in particular preferably comprises the mixture of glyceryl dibenenate, tribehenin and glyceryl behenate. Such a mixture is in particular marketed under the trademark Compritol 888 by Gattefossé. In the remainder of the description of the invention, the expression glyceryl behenate means glyceryl behenate, its derivatives or mixtures thereof. Glyceryl behenate is a thickener for the oily phase. In the compositions according to the invention, glyceryl behenate cakes over time and makes it possible to prepare a hydrophobic composition whose final viscosity is obtained only after a certain time. In the specific case according to the invention, the constituents and the method are effectively selected so as to confer fluidity on the composition immediately after production, facilitating homogenization of the various constituents, but a desired final viscosity about 24 hours following manufacture. To obtain this result, the composition comprises from 1 to 40%, preferably from 5 to 30%, and more preferably still from 10 to 25% by weight relative to the total weight of the glyceryl behenate composition.

The compositions according to the invention may also comprise at least one additional lipophilic gelling agent or thickening agent. Such an additional lipophilic gelling agent or thickening agent gives the composition a better physical stability, in particular when it is subjected to temperatures for accelerated stability conditions (ICH criteria) in the region of 40° C. Indeed, these compounds are employed in the present invention as "viscosity regulators": in particular, by selecting them judiciously, they bring about the stability of the composition at 40° C. This therefore confers a better quality on the compositions obtained.

The expression additional lipophilic thickening agents or gelling agents according to the invention means compounds different from glyceryl behenate, in particular selected from waxes, fatty alcohols, hydrogenated oils, fatty acid esters.

The expression wax means, in general, a lipophilic compound which is solid at room temperature (25° C.), exhibiting a reversible solid/liquid change of state, having a melt point of greater than or equal to 30° C., which may be up to 200° C., and in particular up to 120° C. Exemplary waxes include carnauba wax, microcrystalline waxes, beeswax, which is marketed under the trademark Cerabeil blanche by Barlocher, or alternatively candelilla wax.

Exemplary fatty alcohols include oleyl alcohol, cetyl alcohol, cetearyl alcohol or stearyl alcohol.

The expression hydrogenated oil means the oils obtained by catalytic hydrogenation of animal or vegetable oils having linear or branched $C_8$-$C_{32}$ fatty chains. Among these, there may be mentioned in particular hydrogenated jojoba oil, isomerized jojoba oil such as trans-isomerized partially hydrogenated jojoba oil manufactured or marketed by Desert Whale under the trade reference ISO-JOJOBA-50®, hydrogenated sunflower oil, hydrogenated castor oil, marketed in particular under the trademark Cutina HR by Cognis, hydrogenated copra oil and hydrogenated lanolin oil; hydrogenated castor oil will be preferably used.

Exemplary fatty acid esters include lanolin, marketed in particular under the trademark Medilan by Croda, glyceryl esters of fatty acids marketed under the trademark Gelucire by Gattefossé, hydrogenated coconut glycerides marketed under the trademark Akosoft 36 by Karlshamns, or alternatively diethylene glycol or propylene glycol monostearate, which are marketed respectively under the trademark Hydrine or Monosteol by Gattefossé.

Thus, preferably, the composition comprises an overall quantity of glyceryl behenate and optionally of additional lipophilic thickening agents or gelling agents from 1 to 40% by weight relative to the total weight of the composition, preferably from 5 to 30%. Preferably, the composition comprises 10 to 25% by weight of glyceryl behenate, and 0.5 to 30% by weight of additional lipophilic thickening agent or gelling agent.

Preferably, the compositions according to the invention contain no polyorganosiloxane elastomer, namely any chemically crosslinked siloxane polymer which exhibits viscoelastic properties. Indeed, the viscosity desired for the composition according to the invention is obtained with the aid in particular of glyceryl behenate and the choice of the other fatty substances formulated. The absence of elastomer from the composition makes it possible in particular to introduce more oily compounds, thus conferring the desired emollient properties on the composition. The absence of elastomer makes it possible in particular to obtain the more pronounced effect of glyceryl behenate, namely a fluidity of the composition at the end of manufacture and a final viscosity reached about 24 hours after manufacture.

The composition also comprises at least one solvent for the active agent having a boiling point of greater than 40° C.

The expression solvent having a boiling point of greater than 40° C. means in particular solvents of the alcohol or glycol type or solvents of the oil type. Preferably, the total quality of solvent is from 1 to 50% by weight, preferably from 1 to 20% by weight, more preferably from 5 to 10% by weight relative to the total weight of the composition.

Among the solvents of the alcohol or glycol type which can be employed according to the invention, particularly exemplary are ethanol, diethylene glycol monoethyl ether marketed under the trademark Transcutol by Gattefossé, or alternatively isopropanol, propylene glycol, lauryl alcohol marketed under the trademark Nacol by SPCI, or N-methylpyrrolidone marketed under the trademark Pharmasolve by ISP. According to one of the preferred embodiments according to the invention, the solvent is ethanol.

According to another preferred embodiment according to the invention, the solvent is an oil. Such an oil is preferably selected from:

mineral oils, such as Marcol 152 or Primol 352 marketed by Esso;

triglycerides such as Caprylic/Capric Triglycerides marketed under the trademark Migyol 812 N by SPCI, esters, such as Octyl Dodecyl Myristate marketed under the trademark MOD by Gattefossé, C12-C15 Alkyl benzoate marketed under the trademark Tegosoft TN by Goldschmit or cetearyl Isononanoate marketed under the trademark Cetiol SN PH by Cognis, and mixtures thereof.

Preferably, the solvent oil which can be used according to the invention is mineral oil, capric caprylic triglycerides and cetearyl isononanoate.

In addition to the solvent oil or the alcohol or glycol solvent, those skilled in the art may add another fatty substance selected from the following list:

vegetable oils, such as sweet almond oil marketed by Sictia or sesame oil marketed by CPF, silicone oils such as cyclomethicone marketed under the trademark Mirasil CM5 by Rhodia or Dimethicone marketed under the trademark Q7 9120 silicone fluid by Dow Corning, mineral oils, such as Marcol 152 or Primol 352 marketed by Esso;

perhydrosqualene, triglycerides such as Caprylic/Capric Triglycerides marketed under the trademark Migyol 812 N by SPCI, esters, such as Octyl Dodecyl Myristate marketed under the trademark MOD by Gattefosse, C12-C15 Alkyl benzoate marketed under the trademark Tegosoft TN by Goldschmit or cetearyl Isononanoate marketed under the trademark Cetiol SN PH by Cognis, Guerbet alcohols such as octyldodecanol marketed under the trademark Eutanol G by Cognis, and mixtures thereof.

Indeed, in addition to their solvent property for the active agent for certain of them, these fatty substances may in particular be selected in a variety of ways by one skilled in the art so as to prepare a composition having the desired properties, for example in terms of consistency, texture or for their emollient or moisturizing qualities.

Preferably, the oils are selected from among caprylic/capric triglycerides, cetearyl isononanoate, mineral oil marketed under the trademark Primol 352 by Esso, cyclomethicone marketed under the trademark Mirasil CM5, dimethicone marketed under the trademark Q7 9120 silicone fluid by Dow Corning.

Indeed, mineral oil is an excellent moisturizing agent. Its occlusive properties make it possible to block imperceptible transcutaneous water loss and to trap the water under the surface of the skin, by virtue of the formation of an inert occlusive membrane. This hydrocarbon accelerates the recovery of the normal properties of the skin barrier in the case of lesioned skin, such as for example in atopic dermatitis or psoriasis. The medium chain triglycerides, such as caprylic/capric triglycerides, are selected for their feel which is much less greasy than some vegetable oils. Furthermore, they provide, by virtue of their chemical composition which is close to the fatty acids of the skin, an ideal environment for the penetration of the active agents. Finally, cetearyl isononanoate is an ester which has the characteristic feature of exhibiting a dry and soft feel on the skin.

When at least one oil is present in addition to the solvent oil, their quantity is from 0.05 to 98% by weight, preferably from 1 to 80% by weight.

The compositions according to the invention may also comprise at least one surfactant and/or at least one binder.

The surfactants used are preferably nonionic surfactants, used for example, but not exclusively, to facilitate the incorporation of certain constituents such as glycols into the oily phase of the composition.

Among the surfactants which can be employed according to the invention, exemplary are glyceryl esters and optionally polyethylene glycol esters, such as the mixture of glyceryl stearate and PEG-100 stearate, marketed under the trademark Arlacel 165 by Uniqema, the mixture of glyceryl stearate and PEG-75 stearate, marketed under the trademark Gelot 64 by Gattefossé, glyceryl stearate marketed under the trademark Cutina GMSV by Cognis; emulsifying waxes, such as the self-emulsifying wax marketed under the trademark Polawax NF by Croda, or the beeswax PEG-8 marketed under the trademark Apifil by Gattefossé; polysorbate 80 marketed under the trademark Tween 80 by Uniqema; or alternatively the mixture of glyceryl stearate and PEG-2 stearate, marketed under the trademark Sedefos 75 by Gattefossé. Preferably, polysorbate 80 will be used.

The quantity of surfactants is from 0.1 to 20% by weight, preferably from 1 and 10% by weight.

The composition may also comprise at least one binder. Among the binders which can be employed, exemplary are magnesium stearate marketed by Brentag, maize starch marketed by Roquette, talc marketed by WCD, cholesterol marketed by Croda or silica marketed by Degussa.

The binders may be included in a quantity from 1 and 30% by weight, preferably from 1 to 20% by weight.

To improve the penetration of the active agent(s), absorption promoters may be included in the compositions according to the invention. By way of example of absorption promoters according to the invention, there may be mentioned, in particular, PPG-15 stearyl ether marketed by Uniquema under the trademark Arlamol E, or alternatively myristyl lactate marketed by Croda under the trademark Crodamol, ML.

In a preferred embodiment according to the invention, the incorporation of a base makes it possible to neutralize in particular all acid traces present in certain oils or lipophilic excipients, which acid traces can destabilize the active ingredients derived from vitamin D which can be used in the present invention. The bases which can be included in the composition are in particular triethanolamine, aminomethylpropanol, sodium hydroxide, diisopropanolamine, and preferably triethanolamine.

The compositions according to the invention may also contain additives which those skilled in the art will select according to the effect desired.

Among such additives, exemplary are, taken alone or combined:

antioxidants such as vitamin E and its derivatives, such as DL alpha tocopherol acetate from Roche; vitamin C and its derivatives, such as Ascorbyl Palmitate from Roche, Butyl hydroxytoluene marketed under the trademark Nipanox BHT by Clariant, vitamins such as vitamin PP or niacinamide, soothing agents such as PPG-12/SMDI copolymer marketed by Bertek Pharmaceuticals under the trade name Polyolprepolymer-2 or alternatively glycyrrhetinic acid or its derivatives such as for example Enoxolone marketed by Cognis, moisturizing agents or humectants: exemplary are sugars and derivatives, glycols, glycerine, sorbitol, lectins, cholesterol, preservatives, such as Methylparaben marketed under the trademark Nipagin M by Clariant, Propylparaben marketed under the trademark Nipasol by Clariant, or alternatively phenoxyethanol marketed under the trademark Phenoxetol by Clariant, acids or bases such as citric acid, sodium citrate, triethanolamine, aminomethylpropanol, sodium hydroxide, diisopropanolamine, other additives which make it possible to confer specific properties on the said preparation.

Preferably, the compositions according to the invention comprise, by weight relative to the total weight:

1 to 25% of glyceryl behenate, preferably at least 10%, 1 to 20% of ethanol or solvent liquid oil, 0.5 to 10% of additional lipophilic thickening agent or gelling agent, 1 to 98% of liquid emollient(s), solvent for the active agent or not, 0.0001 to 1% of at least one vitamin D derivative, preferably calcitriol, 0 to 20% of additives.

More preferably, the compositions according to the invention comprise, by weight relative to the total weight:

1 to 20% of glyceryl behenate, preferably at least 10%, 1 to 15% of ethanol or of a solvent liquid oil, 1 to 5% of additional lipophilic thickening agent or gelling agent, 10 to 90% of liquid emollient(s), 0 to 20% of binder(s), 0.0001 to 0.1% of at least one vitamin D derivative, preferably calcitriol, 0 to 10% of additives, in particular of an organic base such as triethanolamine.

More preferably still, the compositions according to the invention comprise, by weight relative to the total weight:

10 to 20% of glyceryl behenate, at least 10%, 1 to 15% of ethanol or of solvent liquid oil, 1 to 80% of liquid emollient(s), 0 to 10% of binder(s), 0.0001 to 0.001% of at least one vitamin D derivative, preferably calcitriol, 0.001 to 0.05% of at least one steroidal anti-inflammatory agent, preferably clobetasol, 0 to 5% of additives, in particular of an organic base such as triethanolamine.

The present invention also features administration of the compositions thus obtained, as medicaments.

More particularly, the composition may be used to formulate a medicament useful for the treatment:

of dermatological conditions linked to a keratinization disorder relating to differentiation and to proliferation, in particular acne vulgaris, comedonal acne, polymorphic acne, acne rosacea, nodulocystic acne, acne conglobata, senile acne, secondary acne such as solar acne, acne medicamentosa or occupational acne, of ichthyosis, ichthyosiform states, Darrier's disease, keratodermia palmaris et plantaris, leukoplakia and leukoplakia-like states, skin or mucosal (buccal) lichen, of dermatological conditions with an inflammatory immunoallergic component with or without a cell proliferation disorder, in particular cutaneous, mucosal or ungual psoriasis, psoriatic rheumatism, skin atopy, such as eczema, respiratory atopy, atopic dermatitis or gingival hypertrophy, of benign or malignant dermal or epidermal proliferations, of viral or nonviral origin, in particular verruca vulgaris, verruca plana, epidermodysplasia verruciformis, oral or florid papillomatosis, T lymphoma, of proliferations which may be induced by ultraviolet radiation, in particular of basal cell or squamous cell epithelioma, of cutaneous precancerous lesions, in particular keratocanthomas, of immune dermatosas, in particular lupus erythematosus, of bullous immune diseases, of collagen diseases, in particular scleroderma, of dermatological or general conditions with an immunological component, of skin disorders due to exposure to UV radiation, of photoinduced or chronological skin aging or of actinic pigmentations and keratoses, or any pathologies associated with chronological or actinic aging, in particular xerosis, of sebaceous function disorders, in particular acne hyperseborrhoea, simple seborrhoea or seborrhoeic dermatitis, of cicatrisation disorders or of stretch marks, of lipid metabolism conditions, such as obesity, hyperlipidemia, non-insulin-dependant diabetes or syndrome X, of inflammatory conditions such as arthritis, of cancerous or precancerous states, of alopecia of different origins, in particular alopecia caused by chemotherapy or radiation, of immune system disorders, such as asthma, type I diabetes mellitus, multiple sclerosis, or other selective dysfunctions of the immune system, or of cardiovascular system conditions such as arteriosclerosis or hypertension.

The anhydrous unguents according to the invention, although containing no petroleum jelly, are particularly useful for the treatment of psoriasis. Indeed, psoriasis is characterized by skin dryness accompanied by thickening of the horny layer. With the aid of the unguent according to the invention, this dryness is reduced by providing emollience.

The compositions according to the invention are also particularly suitable for the treatment of atopic dermatitis and in particular in children when use is preferably made of an oil type solvent, and any other compound providing emollience.

Finally, the present invention also features a method for formulating the subject compositions. Such a method makes it possible in particular to maintain the compositions in a fluid state after manufacture. One of the essential characteristics of the method for preparing the compositions according to the invention being the incorporation of the active phase at room temperature, that is to say that the final step of mixing the phases is carried out at room temperature.

The expression room temperature means a temperature from 20 to 30° C.

In the method according to the invention, the expression active phase means a containing at least one active ingredient. Likewise, in the method according to the invention, the expression non-active phase means a phase consisting of any other ingredient different from the active ingredient. In the compositions according to the invention, the non-active phase is preferably an oily phase containing at least glyceryl behenate, preferably with another oil compound as described above.

Advantageously, the method according to the invention comprises the following steps:

a) preparation of the non-active phase: the glyceryl behenate is mixed with the other constituents of the non-active phase. This mixing requires heating to make the various constituents of the phase fluid. Certain volatile compounds entering into the composition of this phase may be introduced, with stirring, at around 40° C. As soon as the mixture is prepared, it is cooled to room temperature. One of the characteristics of this phase is the maintaining of the compounds in the fluid state despite the cooling to room temperature;

b) preparation of the active phase: the active agent(s) is (are) mixed with its (their) respective solvent(s) having a boiling point of greater than 40° C., these constituents being potentially sensitive to heat and/or inflammable;

c) the active and non-active phases are then mixed at room temperature to obtain a homogeneous composition;

d) the composition obtained is allowed to stand for a period of time necessary to obtain a composition having a viscosity as defined in the present application. Preferably, the composition is allowed to stand for at least 16, preferably 24 h. In particular, the composition has, after at least 24 h, the final viscosity of an unguent.

When the composition also comprises a steroidal anti-inflammatory agent, the method comprises either the direct introduction of this anti-inflammatory agent into the solution obtained in step b), or a step of mixing at least one steroidal anti-inflammatory agent with a solvent, until a solution is obtained, and then the introduction of this solution into the mixture of step c).

Preferably, the method of manufacture comprises the following steps:

a) preparation of the non-active phase: the glyceryl behenate and the compounds different from the solvents and the active agents, preferably the oily compounds, and/or the waxes and other potential additives are mixed, with slow stirring, at the temperature required for melting, preferably at a temperature of at least 60° C. One skilled in the art will adjust the heating temperature to the nature of the constituents to be mixed. Some volatile compounds entering into the composition of this phase may be introduced, with stirring, at around 40° C. The mixture obtained, comprising the compounds different from the solvents and the active agents, is cooled by one of the means that are available to one skilled in the art, preferably allowed to cool, with gentle stirring, at room temperature, or until room temperature is reached;

b) preparation of the active phase: the vitamin D derivative is mixed with its alcoholic solvent, namely preferably ethanol, or oily solvent, namely preferably a mineral oil, a triglyceride or an ester;

c) the active phase is then incorporated into the non-active phase, with gentle stirring, at room temperature;

d) the final viscosity of the composition is measured after at least 24 h.

The expression slow stirring according to the invention means stirring carried out by means of a Rayneri type stirrer, at a speed of from 100 and 300 revolutions/minute.

The expression gentle stirring according to the invention means stirring carried out by means of a Rayneri type stirrer at a speed of from 301 to 600 revolutions/minute.

The method confers the following advantages on the product:

good homogeneity of the active agents because all the components are mixed in a fluid phase, the absence of encrusting phenomenon during cooling and good fluidity of the product up to the end of manufacture, easy packaging due to the small volume at the end of manufacture, the final viscosity of the composition of the unguent type being reached only after about 24 h, the mixing carried out at room temperature avoids the volatilization of the solvent(s) and the degradation of the heat-sensitive active agent and in particular the vitamin D derivative, such as calcitriol.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Solubilities and Stabilities of the Active Agents a) Solubility of Clobetasol Propionate:

| Solvent | Solubility | Method |
| --- | --- | --- |
| Ethanol 96 | 50.40 mg/g | HPLC |
| Transcutol | 120.70 mg/g | HPLC |
| Propylene glycol | 9.10 mg/g | HPLC | b) Stability of Calcitriol in Ethanol:

Calcitriol solution 30 ppm in qs 100% absolute ethanol in the presence of 0.02% BHT.

Assay technique by HPLC against a reference substance. The starting time (T0) is considered to be 100%.

| Stability conditions | T1 week | T2 weeks | T3 weeks | T4 weeks |
| --- | --- | --- | --- | --- |
| −18° C. | 100.9% | 100.5% | 99.5% | 99.5% |
| +4° C. | 97.7% | 98.6% | 98.1% | 97.7% |
| +30° C. | / | 93.4% | / | 93.0% |

Example 2

Method for Preparing the Compositions a) Preparation of the Fatty Phase or Non-Active Phase:

All the oil and consistency factor constituents are introduced into the manufacturing beaker. The mixture is subjected to stirring in the hot state to obtain homogeneous melting of the ingredients. The fatty phase additives are added if necessary, and then the mixture is cooled to room temperature, with gentle stirring.

The volatile compounds, when present, are incorporated into the composition at around 40° C.

B) Active Phase:

A stock solution of the vitamin D compound is prepared in a suitable solvent, an antioxidant is added if necessary and the mixture is stirred until the active agent is solubilized.

If a second active agent is present in the composition, for example a corticoid, weigh the corticoid and its solvent at this stage and stir until the active agent is solubilized.

The active phase(s) is (are) incorporated into the formula base below 30° C., with Rayneri stirring.

The additional phases are incorporated if necessary.

Homogenization is carried out and cooling is continued with Rayneri stirring.

The conditioning is carried out at the end of the manufacture because the product does not yet have its final viscosity.

Example 3

| Phases | INCI name | % Formula |
| --- | --- | --- |
| A | Glyceryl behenate | 10.00 |
| A | Hydrogenated castor oil | 3.00 |
| A | Cetearyl isononanoate | qs 100 |
| A | Mineral oil | 41.00 |
| B | Ethanol 100 | 6.00 |
| B | BHT | 0.04 |
| B | Calcitriol | 0.0003 |
| B | Clobetasol 17-propionate | 0.05 |

Assessments of the Viscosity of the Vehicle:

Method:

Brookfield RVDVII+

Rotor 4

Speed: 30 rpm

Time: 30 s

Temperature: 25° C.

Viscosity at the end of manufacture: 15 737 cps

Viscosity at RT at T24H: 95 991 cps

Specifications at T0:

Macroscopic appearance: thick and soft unguent, white with slight yellow glints.

Microscopic appearance: absence of calcitriol and clobetasol 17-propionate crystals.

Stabilities:

For all the formulations, the physical stability is measured by macroscopic and microscopic examination of the formulation at room temperature, at 4° C. and at 40° C. after 1 month, 2 months and 3 months and 6 months.

At ambient temperature, the macroscopic examination makes it possible to ensure the physical integrity of the products and the microscopic examination makes it possible to check that there is no recrystallization of the solubilized active agent.

At 4° C., the microscopic examination verifies the non-recrystallization of the solubilized active agents.

At 40° C., the macroscopic examination verifies the integrity of the finished product.

The chemical stability is measured by assaying the active agents by external calibration by HPLC and the results are expressed as % recovery relative to the theoretical value.

Physical Stability:

| Stability conditions | Time | | | |
|---|---|---|---|---|
| | T 1 month | T 2 months | T 3 months | T 6 months |
| RT | Conforms to the specifications | Conforms to the specifications | Conforms to the specifications | Conforms to the specifications |
| +4° C. | Conforms to the specifications | Conforms to the specifications | Conforms to the specifications | Conforms to the specifications |
| 40° C. | Conforms to the specifications | Conforms to the specifications | Conforms to the specifications | Conforms to the specifications |

Chemical Stability:

❧ Calcitriol

| Stability conditions | Time | | |
|---|---|---|---|
| | T 1 month | T 2 months | T 3 months |
| RT | 91.7% | 95.4% | 92.2% |
| 40° C. | 96.6% | 98.2% | 97.5% |

❧ Clobetasol 17-Propionate

| Stability conditions | Time | | |
|---|---|---|---|
| | T 1 month | T 2 months | T 3 months |
| RT | 96.3% | 97.2% | 95.1% |
| 40° C. | 93% | 97.6% | 97.8% |

Example 4

| Phases | INCI name | % Formula |
|---|---|---|
| A | Glyceryl behenate | 5.00 |
| A | Hydrogenated castor oil | 5.00 |
| A | Cetearyl isononanoate | qs 100 |
| A | Mineral oil | 45.00 |
| B | Ethanol 100 | 6.00 |
| B | BHT | 0.04 |
| B | Calcitriol | 0.0003 |
| B | Clobetasol 17-propionate | 0.05 |

Specifications at T0:

Macroscopic appearance: thick and soft lipogel, white with slight yellow glints.

Microscopic appearance: absence of calcitriol and clobetasol 17-propionate crystals.

Physical Stability:

| Stability conditions | Time | | |
|---|---|---|---|
| | T 1 month | T 2 months | T 3 months |
| RT | Conforms to the specifications | Conforms to the specifications | Conforms to the specifications |
| +4° C. | Conforms to the specifications | Conforms to the specifications | Conforms to the specifications |

| Stability conditions | Time | | |
|---|---|---|---|
| | T 1 month | T 2 months | T 3 months |
| 40° C. | Conforms to the specifications | Conforms to the specifications | Conforms to the specifications |

Chemical Stability:

❧ Calcitriol

| Stability conditions | Time | | |
|---|---|---|---|
| | T 1 month | T 2 months | T 3 months |
| RT | 117% | 113.4% | In progress |
| 40° C. | 116.4% | 114.3% | In progress |

❧ Clobetasol 17-Propionate

| Stability conditions | Time | | |
|---|---|---|---|
| | T 1 month | T 2 months | T 3 months |
| RT | 110.8% | 109% | In progress |
| 40° C. | 112.3% | 109.4% | In progress |

Example 5

| Phases | INCI name | % Formula |
|---|---|---|
| A | Glyceryl behenate | 10.00 |
| A | PVP eicosene copolymer (consistency additive) | 3.00 |
| A | Cetearyl isononanoate | qs 100 |
| A | Mineral oil | 41.00 |
| B | Ethanol 100 | 6.00 |
| B | BHT | 0.04 |
| B | Calcitriol | 0.0003 |
| B | Clobetasol 17-propionate | 0.05 |

Specifications at T0:

Macroscopic appearance: thick and soft lipogel, white with slight yellow glints.

Microscopic appearance: absence of calcitriol and clobetasol 17-propionate crystals.

Example 6

| Phases | INCI name | % Formula |
|---|---|---|
| A | Glyceryl behenate | 10.00 |
| A | Magnesium stearate | 2.00 |
| A | Cetearyl isononanoate | qs 100 |
| A | Mineral oil | 40.00 |
| B | Ethanol 100 | 6.00 |
| B | BHT | 0.04 |
| B | Calcitriol | 0.0003 |
| B | Clobetasol 17-propionate | 0.05 |

Specifications at T0:

Macroscopic appearance: thick and soft lipogel, white with slight yellow glints.

Microscopic appearance: absence of calcitriol and clobetasol 17-propionate crystals.

Example 7

| Phases | INCI name | % Formula |
|---|---|---|
| A | Glyceryl behenate | 10.00 |
| A | Hydrogenated castor oil | 3.00 |
| A | Capric/caprylic triglycerides | qs 100 |
| A | Mineral oil | 30.00 |
| B | Ethanol 100 | 6.00 |
| B | BHT | 0.04 |
| B | Calcitriol | 0.0003 |
| B | Clobetasol 17-propionate | 0.05 |

Specifications at T0:

Macroscopic appearance: thick and soft lipogel, white with slight yellow glints.

Microscopic appearance: absence of calcitriol and clobetasol 17-propionate crystals.

Physical Stability:

| Stability conditions | Time | | |
|---|---|---|---|
| | T 1 month | T 2 months | T 3 months |
| RT | Conforms to the specifications | In progress | In progress |
| +4° C. | Conforms to the specifications | In progress | In progress |
| 40° C. | Conforms to the specifications | In progress | In progress |

Example 8

| Phases | INCI name | % Formula |
|---|---|---|
| A | Glyceryl behenate | 10.00 |
| A | Glyceryl stearate and PEG-100 stearate | 5.00 |
| A | Cetearyl isononanoate | qs 100 |
| A | Mineral oil | 37.00 |
| A | Water | 5.00 |
| B | Ethanol 100 | 6.00 |
| B | BHT | 0.04 |
| B | Calcitriol | 0.0003 |
| B | Clobetasol 17-propionate | 0.05 |

Example 9

| Phases | INCI name | % Formula |
|---|---|---|
| A | Glyceryl behenate | 10.00 |
| A | Glyceryl stearate and PEG-100 stearate | 5.00 |
| A | Cetearyl isononanoate | qs 100 |
| A | Mineral oil | 37.00 |
| | Propylene glycol | 5.00 |
| B | Ethanol 100 | 9.50 |
| B | BHT | 0.04 |
| B | Calcitriol | 0.0003 |
| B | Clobetasol 17-propionate | 0.05 |

Example 10

| Phases | INCI name | % Formula |
|---|---|---|
| A | Glyceryl behenate | 15.00 |
| A | Hydrogenated castor oil | 2.00 |
| A | Cetearyl isononanoate | 10.00 |
| A | Mineral oil | 41.00 |
| A | Capric caprylic triglycerides | qs 100 |
| A | Triethanolamine | 1.00 |
| B | Ethanol 100 | 6.00 |
| B | BHT | 0.04 |
| B | Calcitriol | 0.0003 |

Example 11

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 1.00 |
| A | Capric caprylic triglycerides | qs 100 |
| A | PPG-15 stearyl ether | 2.5 |
| A | Myristyl lactate | 5 |
| B | Cyclopentasiloxane | 12 |
| B | Ethanol 100 | 10.00 |
| B | BHT | 0.04 |
| B | Calcitriol | 0.0003 |

Example 12

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 1.00 |
| A | Cyclopentasiloxane | 22 |
| A | Capric caprylic triglycerides | qs 100 |
| A | PPG-15 stearyl ether | 2.5 |
| A | Myristyl lactate | 5 |
| B | BHT | 0.04 |
| B | Calcitriol | 0.003 |
| B | Capric caprylic triglycerides | 10 |

Example 13

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 1.00 |
| A | Cyclopentasiloxane | 22 |
| A | Capric caprylic triglycerides | qs 100 |
| A | PPG-15 stearyl ether | 2.5 |
| A | Myristyl lactate | 5 |
| B | BHT | 0.04 |
| B | Calcitriol | 0.0003 |
| B | Capric caprylic triglycerides | 3.5 |

Example 14

| Phases | INCI name | % Formula |
|---|---|---|
| A | Glyceryl behenate | 15.00 |
| A | Hydrogenated castor oil | 2.00 |
| A | Dimethicone | 2 |
| A | Mineral oil | 10 |
| A | Triethanolamine | 0.1 |
| A | Cyclopentasiloxane | 22 |
| A | Capric caprylic triglycerides | qs 100 |
| B | BHT | 0.04 |
| B | Calcitriol | 0.0003 |
| B | Cetearyl isononanoate | 13.5 |

Example 15

| Phases | INCI name | % Formula |
|---|---|---|
| A | Glyceryl behenate | 15.00 |
| A | Hydrogenated castor oil | 2.00 |
| A | Cetearyl isononanoate | 12 |
| A | Triethanolamine | 0.1 |
| A | Cyclopentasiloxane | 22 |

-continued

| Phases | INCI name | % Formula |
|---|---|---|
| A | Capric caprylic triglycerides | qs 100 |
| B | BHT | 0.04 |
| B | Calcitriol | 0.0003 |
| B | Mineral Oil | 3.5 |

Example 16

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 0.1 |
| A | Cyclopentasiloxane | 12 |
| A | Capric caprylic triglycerides | qs 100 |
| B | BHT | 0.04 |
| B | Calcitriol | 0.0003 |
| B | Ethanol | 10 |

Example 17

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 1.00 |
| A | Cyclopentasiloxane | 22 |
| A | Capric caprylic triglycerides | qs 100 |
| A | PPG-15 stearyl ether | 2.5 |
| A | Myristyl lactate | 5 |
| B | BHT | 0.04 |
| B | Calcitriol | 0.0015 |
| B | Capric caprylic triglycerides | 13.5 |

Example 18

| Phases | INCI name | % Formula |
|---|---|---|
| A | Glyceryl behenate | 15.00 |
| A | Hydrogenated castor oil | 2.00 |
| A | Mineral oil | 25 |
| A | Triethanolamine | 0.1 |
| A | Cyclopentasiloxane | 12 |
| A | Capric caprylic triglycerides | qs 100 |
| B | BHT | 0.04 |
| B | Calcitriol | 0.001 |
| B | Ethanol | 10 |

Example 19

| Phases | INCI name | % Formula |
|---|---|---|
| A | Glyceryl behenate | 15.00 |
| A | Hydrogenated castor oil | 2.00 |
| A | Cetearyl isononanoate | 10.00 |
| A | Mineral oil | 41.00 |
| A | Capric caprylic triglycerides | qs 100 |
| A | Triethanolamine | 1.00 |
| B | Ethanol 100 | 6.00 |
| B | BHT | 0.04 |
| B | Calcitriol | 0.0015 |

Example 20

| Phases | INCI name | % Formula |
|---|---|---|
| A | Glyceryl behenate | 15.00 |
| A | Hydrogenated castor oil | 2.00 |
| A | Cetearyl isononanoate | 10.00 |
| A | Mineral oil | 41.00 |
| A | Capric caprylic triglycerides | qs 100 |
| A | Triethanolamine | 1.00 |
| A | Polysorbate 80 | 0.2 |
| A | Propylene glycol | 2 |
| B | Ethanol 100 | 6.00 |
| B | BHT | 0.04 |
| B | Calcitriol | 0.0015 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An anhydrous unguent composition, comprising by weight relative to the total weight thereof:
   a) 0.00001 to 5% of at least one vitamin D compound, selected from the group consisting of calcipotriol, calcitriol, doxercalciferol, secalcitol, maxacalcitol, seocalcitol, tacalcitol, paricalcitol, falecalcitriol, 1α,24S-dihydroxyvitamin D2, 1(S),3(R)-dihydroxy-20(R)-[((3-(2-hydroxy-2-propyl)phenyl)methoxy)methyl]-9,10-secopregna-5(Z),7(E),10(19)triene, and {4-[6-ethyl-4'-(1-ethyl-1-hydroxypropyl)-2'-propylbiphenyl-3-yloxymethyl]-2-hydroxymethylphenyl}methanol,
   b) 10 to 40% of glyceryl behenate,
   c) 1 to 50% of alcohol, glycol, and/or oil having a boiling point greater than 40° C., and
   d) 0.5 to 10% of an additional lipophilic thickening agent or gelling agent, wherein the composition contains no petroleum jelly or polyorganosiloxane elastomer.

2. The unguent composition as defined by claim 1, further comprising at least one additional fatty substance.

3. The unguent composition as defined by claim 1, said vitamin D compound is calcitriol.

4. The unguent composition as defined by claim 3, wherein the calcitriol is present in a quantity from 0.0001 to 1% by weight relative to the total weight of the composition.

5. The unguent composition as defined by claim 1, further comprising at least one steroidal anti-inflammatory agent.

6. The unguent composition as defined by claim 5, wherein said at least one steroidal anti-inflammatory agent is selected from the group consisting of betamethasone, clobetasol, clobetasone, desoxymethasone, diflucortolone, diflorasone, fluocinonide, flumethasone, fluocinolone, fluticasone, fluprednidene, halcinonide, hydrocortisone, mometasone, triamcinolone, and the pharmaceutically acceptable esters and acetonides thereof.

7. The unguent composition as defined by claim 6, said at least one steroidal anti-inflammatory agent comprising clobetasol propionate.

8. The unguent composition as defined by claim 7, wherein the clobetasol propionate is present in a quantity from 0.0001 to 10% by weight relative to the total weight of the composition.

9. The unguent composition as defined by claim 1, wherein said at least one additional lipophilic thickening agent or gelling agent is selected from among oleyl alcohol, cetyl alcohol, cetearyl alcohol, stearyl alcohol, hydrogenated jojoba oil, hydrogenated sunflower oil, hydrogenated castor oil, hydrogenated copra oil, hydrogenated lanolin oil, lanolin, glyceryl esters of fatty acids, hydrogenated coconut glycerides, and diethylene glycol or propylene glycol monostearate.

10. The unguent composition as defined by claim 1, further comprising at least one surfactant, and/or at least one oil and/or at least one binder.

11. The unguent composition as defined by claim 10, wherein said at least one oil is selected from the group consisting of vegetable oils, mineral oils, silicone oils, caprylic/capric triglycerides, octyl dodecyl myristate, C12-C15 alkyl benzoate, cetearyl isononanoate, and mixtures thereof.

12. The unguent composition as defined by claim 1, further comprising, by weight relative to the total weight thereof:
   e) 1 to 98% of liquid emollient(s), and
   f) 0 to 20% of additives.

13. The unguent composition as defined by claim 12, further comprising, by weight relative to the total weight thereof:
   g) 0 to 20% of binder(s).

14. The unguent composition as defined by claim 1, further comprising by weight relative to the total weight thereof:
   e) 1 to 80% of liquid emollient(s), and
   f) 0.001 to 0.05% of at least one steroidal anti-inflammatory agent.

15. The unguent composition as defined by claim 1, further comprising a pharmaceutical active agent.

16. The unguent composition as defined by claim 1, wherein the alcohol is ethanol.

17. The unguent composition as defined by claim 1, wherein the oil is cetearyl isononanoate.

18. The unguent composition as defined by claim 12, comprising, by weight relative to the total weight thereof:
   a) 0.0001 to 1% of at least one vitamin D compound,
   b) 10 to 25% of glyceryl behenate,
   c) 1 to 20% of ethanol or solvent liquid oil,
   d) 0.5 to 10% of additional lipophilic thickening agent or gelling agent,
   e) 1 to 98% of liquid emollient(s), and
   f) 0 to 20% of additives.

19. The unguent composition as defined by claim 13, comprising, by weight relative to the total weight thereof:
   a) 0.0001 to 0.1% of at least one vitamin D compound,
   b) 10 to 20% of glyceryl behenate, c) 1 to 15% of ethanol or of a solvent liquid oil,
d) 1 to 5% of additional lipophilic thickening agent or gelling agent,
e) 10 to 90% of liquid emollient(s),
f) 1 to 10% of additives, and
g) 0 to 20% of binder(s).

20. The unguent composition as defined by claim 14, comprising by weight relative to the total weight thereof:
a) 0.0001 to 0.001% of at least one vitamin D compound,
b) 10 to 20% of glyceryl behenate,
c) 1 to 15% of ethanol or of solvent liquid oil,
d) 1 to 5% of additional lipophilic thickening agent or gelling agent,
e) 1 to 80% of liquid emollient(s), and
f) 0.001 to 0.05% of at least one steroidal anti-inflammatory agent.

21. An anhydrous unguent composition comprising, by weight relative to the total weight thereof:
0.0001 to 0.1% calcitriol,
10 to 20% glyceryl behenate,
1 to 50% ethanol and/or liquid oil,
0.5 to 10% of an additional lipophilic thickening agent or gelling agent,
1 to 98% liquid emollient(s), and
0 to 20% additives.

22. The unguent composition as defined by claim 21, wherein the composition further comprises an absorption promoter.

23. The unguent composition as defined by claim 21, comprising, by weight relative to the total weight thereof:
15% glyceryl behenate,
2% hydrogenated castor oil,
10% cetearyl isononanoate,
41% mineral oil,
1.0% triethanolamine,
6% ethanol,
0.04% BHT,
0.0003% calcitriol, and
qs 100% capric caprylic triglycerides.

24. The unguent composition as defined by claim 22, comprising, by weight relative to the total weight thereof:
15% glyceryl behenate,
2% hydrogenated castor oil,
25% mineral oil,
1.0% triethanolamine,
2.5% PPG-15 stearyl ether,
5% myristyl lactate,
12% cyclopentasiloxane
10% ethanol,
0.04% BHT,
0.0003% calcitriol and
qs 100% capric caprylic triglycerides.

* * * * *